United States Patent
Chen et al.

(10) Patent No.: US 9,579,069 B2
(45) Date of Patent: Feb. 28, 2017

(54) WEARABLE DEVICE, ELECTRONIC APPARATUS AND METHOD FOR RECORDING USER ACTIONS

(71) Applicant: Wistron Corporation, New Taipei (TW)

(72) Inventors: Li-Hsuan Chen, New Taipei (TW); Po-Hsu Chen, New Taipei (TW)

(73) Assignee: Wistron Corporation, New Taipei (TW)

( * ) Notice: Subject to any disclaimer, the term of this patent is extended or adjusted under 35 U.S.C. 154(b) by 332 days.

(21) Appl. No.: 14/312,692

(22) Filed: Jun. 24, 2014

(65) Prior Publication Data

US 2015/0257711 A1 Sep. 17, 2015

(30) Foreign Application Priority Data

Mar. 11, 2014 (TW) .............................. 103108423 A

(51) Int. Cl.
*A61B 5/103* (2006.01)
*A61B 5/00* (2006.01)
(Continued)

(52) U.S. Cl.
CPC ............... *A61B 5/7282* (2013.01); *A61B 5/11* (2013.01); *A61B 5/1126* (2013.01);
(Continued)

(58) Field of Classification Search
CPC .......... A61H 7/00; A61H 7/007; A61H 7/008; A61H 9/00; A61H 9/005; A61H 9/0078; A61H 9/0092; A61H 2201/00; A61H 2201/0157; A61H 2201/02; A61H 2201/0207; A61H 2201/0214; A61H 2201/5058; A61H 2201/5071; A61H 2201/5074; A61H 2201/5082; A61H 2300/00; A61H 2230/50; A61H 2230/505; A61H 2201/164; A61H 2201/165; A61B 5/7282; A61B 5/11; A61B 5/6831; A61B 5/1126; A61B 5/6804
See application file for complete search history.

(56) References Cited

U.S. PATENT DOCUMENTS 7,947,003 B2 5/2011 Bonnefin et al.
8,517,963 B2 * 8/2013 Larson ............... A61B 17/1325
600/16

(Continued)

FOREIGN PATENT DOCUMENTS

TW M453181 5/2013
TW M471348 2/2014

OTHER PUBLICATIONS

"Office Action of Taiwan Counterpart Application" with partial English translation, issued on Jun. 16, 2016, p. 1-p. 9.

*Primary Examiner* — Steven Douglas
(74) *Attorney, Agent, or Firm* — Jianq Chyun IP Office

(57) ABSTRACT

A wearable device, an electronic apparatus and a method for recording user actions are provided. The wearable device includes a body, at least one sensor and a memory module. An outer part of the body includes a surface, and an internal part includes an accommodating space. The sensor senses touching actions of a user to the surface, and records the location, the force and the number of the touching actions with respective to the surface, so as to form touching information corresponded to the touching actions. Thus, when the user is dressed the wearable device, the sensor senses and stores instinctive physical touching actions of the user relative to the user body covered by the wearable device, and the touching actions can become the basis of the diagnosis by the doctor.

6 Claims, 3 Drawing Sheets

(51) Int. Cl.
 *A61B 5/11* (2006.01)
 *A61M 5/172* (2006.01)
 *A61H 7/00* (2006.01)

(52) U.S. Cl.
 CPC .......... *A61B 5/6831* (2013.01); *A61B 5/6804* (2013.01); *A61H 7/007* (2013.01); *A61H 2201/164* (2013.01); *A61H 2201/165* (2013.01); *A61M 5/1723* (2013.01)

(56) References Cited

U.S. PATENT DOCUMENTS

| | | | | |
|---|---|---|---|---|
| 2007/0255187 | A1* | 11/2007 | Branch | A61F 7/02 601/15 |
| 2012/0116251 | A1* | 5/2012 | Ben-Shalom | A61B 5/11 600/587 |
| 2013/0237889 | A1* | 9/2013 | Wright | A61H 9/0078 601/149 |
| 2015/0297437 | A1* | 10/2015 | Neuenhahn | A61B 5/4848 601/148 |
| 2016/0030279 | A1* | 2/2016 | Driscoll | A61H 19/40 601/15 |
| 2016/0030281 | A1* | 2/2016 | Shafieloo | A61H 23/0263 601/48 |

* cited by examiner

WEARABLE DEVICE, ELECTRONIC APPARATUS AND METHOD FOR RECORDING USER ACTIONS

CROSS-REFERENCE TO RELATED APPLICATION

This application claims the priority benefit of Taiwan application serial no. 103108423, filed on Mar. 11, 2014. The entirety of the above-mentioned patent application is hereby incorporated by reference herein and made a part of this specification.

BACKGROUND OF THE INVENTION

1. Field of the Invention

The invention relates to an application technology of a wearable device, and more particularly, to a wearable device, an electronic apparatus disposed on a body and a method for recording user actions.

2. Description of Related Art

Due to aging or injury, many people often wear protective gears the from time to time so as to protective specific parts of the body, such as knees, legs and so forth. When the body parts located in the internal portions of the protective gears still feel uncomfortable, people would instinctively perform actions such as tapping and kneading with expectations of getting instant relieve.

However, conventional protective gear only provides physical oppression and protection to the body parts that wear the protective gear, but does not automatically perform an adaptive adjustment with respective to user reactions, so that the user can merely adjust the protective gear manually so as to provide better comfort to the body parts that wear the protective gear. On the other hand, when patients describe injury locations to the physicians, such as similar injuries at the knee, it is to be noted that different sites of pain at the knee may be caused by different diseases (e.g., patella tendinitis, cartilage tissue pain, or so forth). However, the patients would all describe these pains as knee pains, and cause the physicians to have difficulty in diagnosing the causes quickly. Since people often instinctively perform physical touching actions, such as tapping, kneading and so forth, to the injured or uncomfortable body parts, it may perhaps be helpful if these instinctive reactions may be transformed into digital information and provided to the physicians, so that the physicians can perform the treatments more accurately based on the digital information.

SUMMARY OF THE INVENTION

The invention provides a wearable device, an electronic apparatus and a method for recording user actions. The wearable device uses sensors to record instinctive touching actions of the user in relative to the user body covered by the wearable device, and transform these touching actions into digital information for diagnosing causes of illness or determining whether the user body wearing the device is comfortable so as to locally enhance an auxiliary function at a specific location.

The invention provides a wearable device. The wearable device includes a body, at least one sensor, a memory module and a processor. The outer part of the body includes a surface, and the internal part of the body includes an accommodating space. The at least one sensor is disposed on the surface. The sensor senses at least one touching action of a user to the surface, and records the location, the force and the number of the touching action with respective to the surface, so as to form at least one touching information corresponded to the touching action. The memory module is coupled to the sensor for storing the touching information.

On the other hand, the invention provides an electronic apparatus adapted to be used in a wearable body. The wearable body includes a surface and an accommodating space. The electronic apparatus includes at least one sensor, a memory module and a processor. The sensor is disposed on the surface of the wearable body, and is used to sense at least one touching action of a user to the surface and recording the location, the force and the number of the touching action with respective to the surface, so as to form at least one touching information corresponded to the touching action. The memory module s coupled to the sensor for storing the touching information. The processor is used to analyze the touching information for executing an operation.

From another point of view, the invention provides a method for recording user actions, which is adapted to be used on a wearable body. The wearable body includes a surface and an accommodating space. The said method includes the following steps. At least one touching action of a user to the surface is sensed. The location, the force and the number of the touching action with respective to the surface are recorded to form at least one touching information corresponded to the touching actions. And, the touching information is stored and analyzed for executing an operation.

In view of the above, the wearable device and the method for recording user actions described in the embodiments of the invention use the sensor on the surface of the wearable device to automatically sense and record the instinctive physical touching actions of the user in relative the user body covered by the wearable device, and provide the information regarding these touching actions to the physicians as basis for diagnosing the causes of illness. As such, the wearable device may become another tool for helping the physicians in performing treatments. On the other hand, a variety of electronic auxiliary devices may also be disposed at the internal side of the wearable device. The processor in the wearable device can determine which specific location of the user body wearing the wearable device is uncomfortable based on these touching actions of the user and locally enhance the auxiliary function at the specific location to perform symptom relief. In other words, the embodiments of the invention enable the user to quickly understand how to use the wearable device based on the instinctive actions. The wearable device may automatically sense and record the actions, such as tapping, kneading and so forth, of the user in relative to the user body wearing the wearable device so as to record the touching habits of the user in relative to the user body, and may provide the records of these touching actions to the physicians and therapists as the basis for diagnosing the causes of illness. The processor in the wearable device may also use an auxiliary module to timely enhance the auxiliary function at the user body wearing the wearable device.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

When a part of the body feels uncomfortable, people are accustomed to instinctive physical movements, such as tapping, kneading and so forth, to get instant physical relief. Hence, in an embodiment of the invention, a plurality of sensors capable sensing pressure level are disposed on a body surface of a clothing, a protective gear or so forth, so that when people perform instinctive physical touching actions, the sensors may sense these touching actions and transform them into digital information for being recorded in a memory module, such as a cache memory. As a result, detail status regarding actions of the user in relative to the user body wearing the clothing or the protective gear, such as kneading a site of pain, pounding a site of soreness or so forth, may be record. The digital information of these touching actions may be outputted to an external storage device, so that physicians, nurses and therapists may use the information of the of these touching actions to determine the illness of the user, and thus the clothing or the protective gear that includes the sensors may be used for information collection during a pre-treatment phase. On the other hand, an auxiliary module with an auxiliary function may further be disposed in an accommodating space of the internal part of the protective gear that includes the sensors, so that when the user body wearing the protective gear experiences soreness, the user may tap a specific location, and the protective gear may provide physical relief targeting the specific location (e.g., helping blood circulation by heating, providing support by inflating an airbag at the specific location, and so forth). As such, the protective gear including the sensors may be used as a wearable device, and each protective gear may also be customized according to the need of each different user. In the following below, several embodiments complying with the spirit of the invention are provided, proper modifications can be made to these embodiments without departing from the scope of the invention; namely, the invention is not limited by the descriptions provided below.

Figure 1:
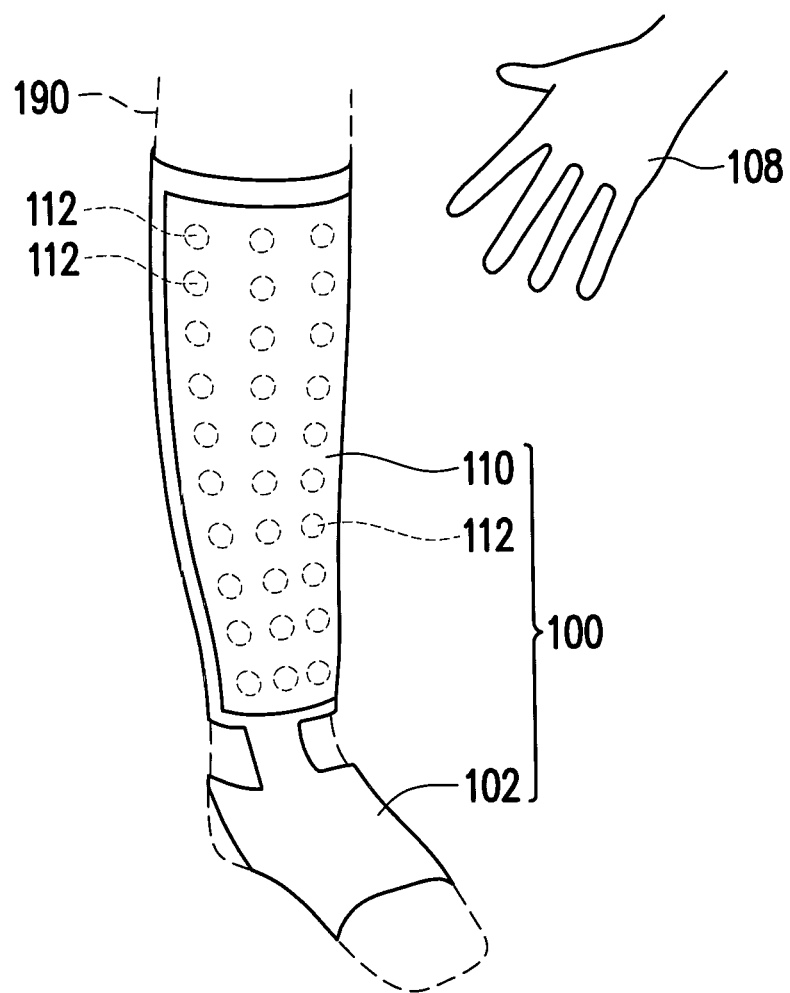
FIG. 1 and FIGS. 2A-2B respectively are schematic diagrams illustrating a wearable device according to an embodiment of the invention.
Figure 2A:
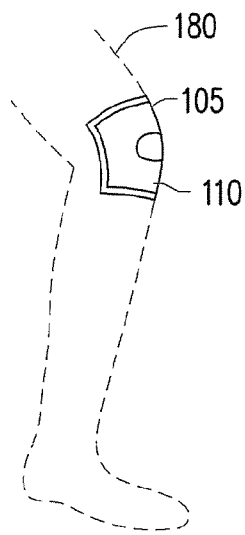
Figure 2B:
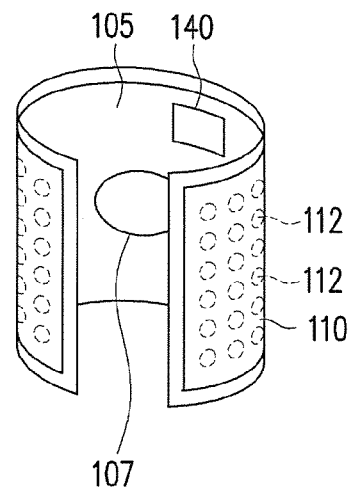
Figure 3:
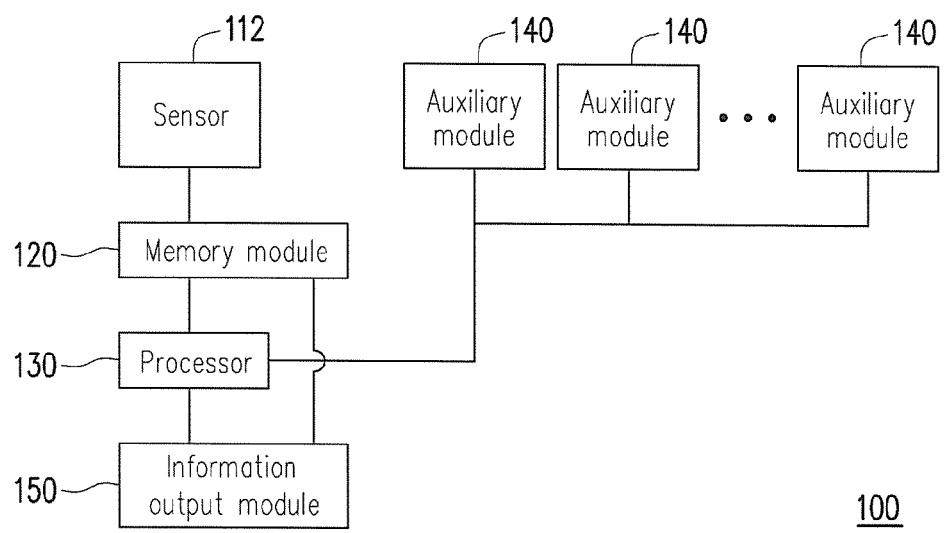
FIG. 3 is a block diagram illustrating a wearable device according to an embodiment of the invention.

FIG. 1 and FIGS. 2A-2B respectively are schematic diagrams illustrating a wearable device according to an embodiment of the invention. FIG. 3 is a block diagram illustrating a wearable device according to an embodiment of the invention. Referring to FIG. 1 through FIG. 3 at the same time, the wearable device 100 mainly includes a body, at least one sensor 110 and a memory module 120. The body may be the clothing or a protective gear worn by a user; and the protective gear has been taken as an example in the present embodiment, but the application of the present embodiment is not limited thereto. The body of the wearable device 100 in FIG. 1 is a protective gear 102 covering from calf to foot. The body of the wearable device in FIGS. 2A-2B is a protective gear 105 used on the knee 180, wherein the knee may flex and extend through a hole 107. The outer part of the body 102, 105 includes a surface 110, and the surface 110 includes at least one sensor 112 thereon.

In the present embodiment, the sensors 112 are circular pressure sensors that are evenly distributed on the surface 110 of the body 102,105; in other embodiments, the sensors 112 may also be sheet-shaped pressure sensors that are tiled on the surface 110 of the body 102, 105; those who adopt the present embodiment in application may adaptively dispose the sensors on the surface 110 of the body 102, 105 based on the shape of the sensors.

In an embodiment complying with the invention, the wearable device 100 may further include a processor 130. The processor 130 is coupled to a memory module 120. The memory module 120 may be a cache memory or a media capable of storing digital information. Processing and interpretation of touching information between the sensors 112, the memory module 120 and the processor 130 may be realized using a grip pressure distribution measurement system, for instance. The grip pressure distribution measurement system may measure the force and the number of touching actions applied to each location. In detail, the grip pressure distribution measurement system may present and record the pressure distribution on the surface 110 in two-dimension or three-dimension, and may show the contact location, the region and the range of the force through peak pressure, power center and movement trajectory of the force, so that the processor 130 may accurately interpret the touching actions of the user, such as kneading, pressing or pouching.

For instance, in FIG. 1, when the calf 109 of the user senses pain, the hand 108 of the user would instinctively perform an action, such as kneading, pouching or massaging, to a location on the protective gear 110 corresponding to the calf 109, and then the pressure sensor 112 would sense the location and the force of this touching action. When the force of this touching action is smaller than a preset value, then it indicates that the user might have inadvertently touched the location of this touching action. Contrarily, when the force of this touching action is greater than a preset value, then it indicates that this touching action is an instinctive physical touching action, and the sensors 112 would transform the location and the force of this touching action into digital touching information so as to be stored in the memory module. In addition, the processor 130 includes a counter therein, so that the processor 130 may use the digital touching information to count the number and the frequency of the touching action that the user has performed on a location, and record the number and the frequency of the touching action in the memory module 120. In an embodiment complying with the invention, the sensors 112 may also include a counter therein, so that the sensors 112 may record the touching actions with respective to the location of the surface 110, the force applied by the user, and the number of touching actions performed in this location per unit of time, so as to form the digital touching information corresponded to these touching actions. The processor 130 may analyze these touching information to execute corresponding operations. The operations may be a plurality of preset operations preset in an operation database of the memory module 120, and these preset operations may output the collected digital touching information to other device through an information output module 150 or may perform symptom relief to the calf 190 through various auxiliary modules 140.

In the present embodiment, the wearable device may further include an information output module 150 coupled to the memory module 120 and the processor 130, as shown in FIG. 3. In the present embodiment, the information output module 150 may be a universal serial bus (USB) port. When an external storage device (such as a USB flash drive) is connected to the information output module 150, the processor 130 may execute the corresponding operations to provide and store the digital touching information in the memory module 120 to the external storage device. As such, the user may obtain the touching action record with respective to the body parts that wear the wearable device, so that medical professionals may use the record as data for diagnosis and treatment, thereby making up for the possible ambiguity and inadequacy in an oral narrative of the user.

On the other hand, the wearable device may further include at least one auxiliary module 140, as shown in FIGS. 2A-2B and FIG. 3. The auxiliary modules 140 are disposed at the internal side of the body 105. The auxiliary modules 140 may be one of temperature control modules, drug projection modules, knead massage modules and airbag filling modules, or a combination thereof. The auxiliary modules 140 are all physical adjustment structures that perform symptom reliefs to the body parts of the user that wear the wearable device. In other words, the processor 130 may further analyze the digital touching information by comparing with a database in-built in the memory module 120 or a comparison table, and thereby automatically determine whether it is required to perform an auxiliary function the user body (such as the calf 190 or the knee 180) in the accommodating space by using the auxiliary module 140. The auxiliary function indicated herein may be to locally use the drug projection module to perform a localized projection (such as pain relief, anti-inflammation and other symptom relief) to the user body, use the temperature control module to locally adjust the temperature of a specific location to perform icing or thermotherapy, use the airbag filling module to perform an airbag filling to the supports of the protective gear so as to adjust a flexibility thereof, or activate the knead massage module at a specific location to relieve fatigue of the user body, etc. Hence, it can be expected that, when using the wearable device and the electronic apparatus disclosed in the embodiments of the invention, the user may produce a user feedback experience of "pounding may make it feel much better when feeling uncomfortable".

From another point of view of the present embodiment, the embodiments of the invention may also use various components other than the body (e.g., including the sensor 112, the memory module 120 and the processor 130) as an electronic apparatus, and design the sensor 112 of this electronic apparatus in a way that it can be easily disposed on the surface of a required wearable body (e.g., the clothing or the protective gear) by the user. As such, this electronic apparatus may also comply with the spirit of the embodiments of the invention. Implementations of the sensor 112, the memory module 120 and the processor 130 are similar to the aforementioned embodiments, and thus are not to be repeated herein. This electronic apparatus may also selectively be added with a signal output module 150 and/or an auxiliary module 140.

Figure 4:
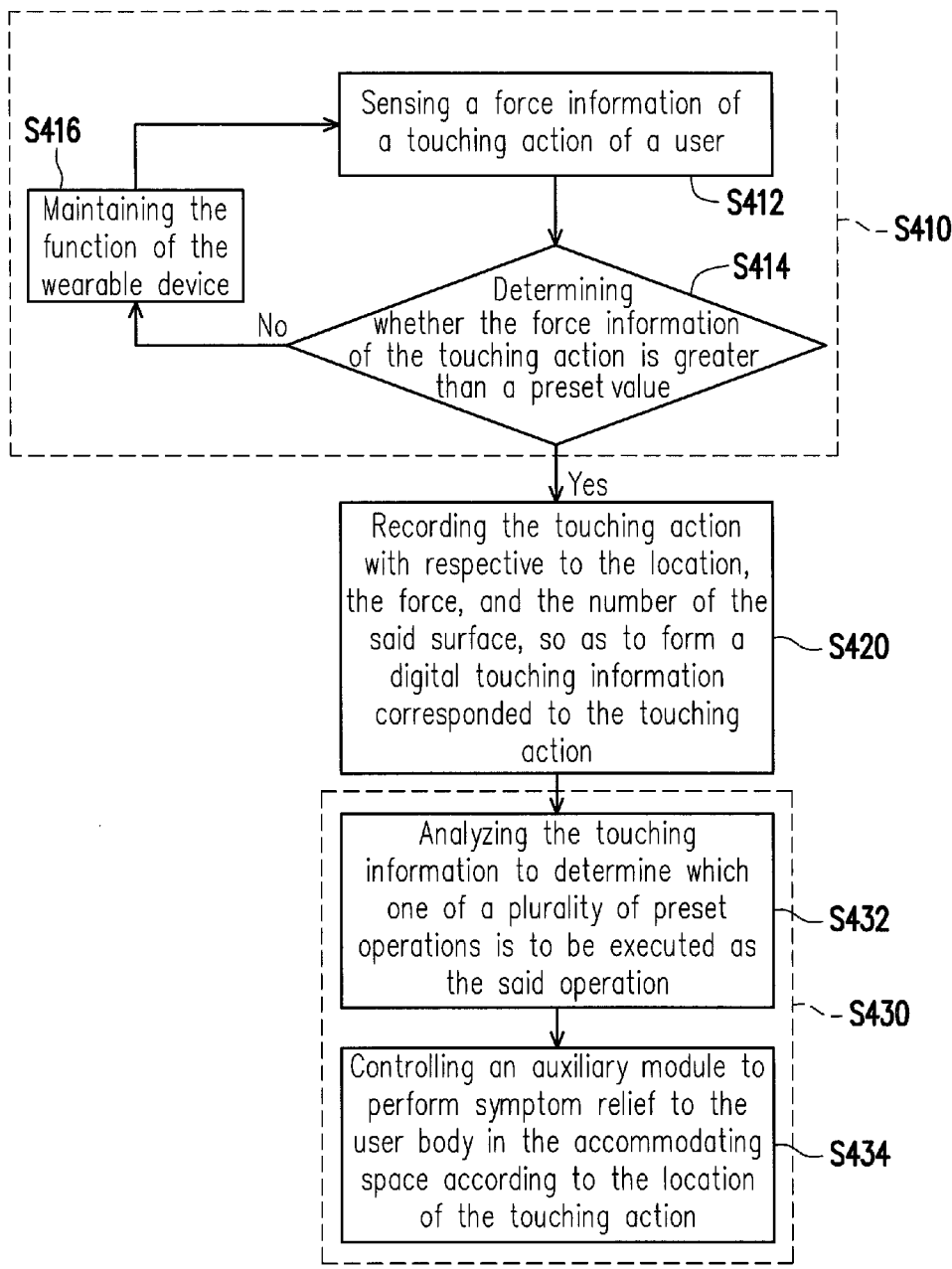
FIG. 4 is a flow chart illustrating a method for recording user actions according to an embodiment of the invention.

FIG. 4 is a flow chart illustrating a method for recording user actions according to an embodiment of the invention. Referring to FIG. 3 and FIG. 4 at the same time, in step S410, the sensor 112 sense at least one touching action of the user to the surface of the body. Detailed process of the step S410 are described herein. In step S412, the sensor 112 sense a force information of a touching action of the user. In step S414, the processor 130 determines whether the force information of the touching action is greater than a preset value. When the force information of the touching action is smaller than the preset value, it indicates that the processor 130 would filter out the force information by considering the touching action as a noise, and then the process would enter from step S414 into step S416, so as to maintain the function of the wearable device (namely, the protective gear). On the other hand, in step S414, when the processor 130 determines the force information of the touching action is greater than the preset value, it indicates that the touching action should be an instinctive physical touching action, and thus the process enters into step S420, such that the sensor 112 records the touching action with respective to the location, the force, and the number of the surface, so as to form a digital touching information corresponded to the touching action.

In step S430, the processor 130 stores the touching information and analyzes the touching information to execute a corresponding operation. Detailed process regarding the step S430 are described herein. In step S432, the processor 130 analyzes the touching information to determine which one of a plurality of preset operations is to be executed as the aforementioned operation. In step S434, the processor 130 controls the at least one auxiliary module 140 to perform symptom relief to the user body in the accommodating space according to the location of the least one touching action, wherein the auxiliary module 140 is located at the side of the accommodating space of the wearable device.

In summary, the wearable device and the method for recording user actions described in the embodiments of the invention use the sensor on the surface of the wearable device to automatically sense and record the instinctive physical touching actions of the user in relative the user body covered by the wearable device, and provide the information regarding these touching actions to the physicians as basis for diagnosing the causes of illness. As such, the wearable device may become another tool for helping the physicians in performing treatments. On the other hand, a variety of electronic auxiliary devices may also be disposed at the internal side of the wearable device. The processor in the wearable device can determine which specific location of the user body wearing the wearable device is uncomfortable based on these touching actions of the user and locally enhance the auxiliary function at the specific location to perform the symptom relief. In other words, the embodiments of the invention enable the user to quickly understand how to use the wearable device based on the instinctive actions. The wearable device may automatically sense and record the actions, such as tapping, kneading and so forth, of the user in relative to the user body wearing the wearable device so as to record the touching habits of the user in relative to the user body, and may provide the records of these touching actions to the physicians and the therapists as the basis for diagnosing the causes of illness. The processor in the wearable device may also use the auxiliary module to timely enhance the auxiliary function at the user body wearing the wearable device.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. A wearable device, comprising:
a body, an outer part of the body comprising a surface, and an internal part of the body comprising an accommodating space;

at least one sensor, disposed on the surface for sensing a location, a force and a number of at least one touching action of a user on the surface to generate at least one touching information corresponded to the at least one touching action, wherein the at least one touching information is a digital signal;

a memory module, coupled to the at least one sensor for storing the at least one touching information;

a processor, analyzing the at least one touching information for executing an operation; and at least one auxiliary module, coupled to the processor, and disposed inside the body, wherein the processor analyzes the touching information to determine which one of a plurality of preset operations is to be executed as the operation, and controls the at least one auxiliary module corresponded to the operation, so as to perform an auxiliary function to the user body in the accommodating space according to the at least one touching information.

2. The wearable device as recited in claim 1, further comprising:

an information output module, coupled to the memory module and the processor, wherein when an external storage device is connected to the information output module, the processor executes the operation via the information output module, so as to provide the at least one touching information to the external storage device.

3. The wearable device as recited in claim 1, wherein the at least one auxiliary module is one of a temperature control module, a drug projection module and a knead massage module, or a combination thereof.

4. The wearable device as recited in claim 1, wherein the body is a clothing or a protective gear.

5. A method for recording user actions, adapted to be used on a wearable body comprising a surface and an accommodating space, the method comprising:

sensing a location, a force and a number of at least one touching action of a user on the surface;

generating at least one touching information corresponded to the at least one touching action, wherein the at least on touching information is a digital signal;

storing the at least one touching information;

analyzing the at least one touching information to determine which one of a plurality of preset operations is to be executed as an operation; and controlling at least one auxiliary module to perform symptom relief to the user body in the accommodating space according to the location of the least one touching action, wherein the at least one auxiliary module is located at the side of the accommodating space of the wearable device.

6. The method as recited in claim 5, wherein the at least one auxiliary module is one of a temperature control module, a drug projection module and a knead massage module, or a combination thereof.

* * * * *